United States Patent [19]
Macevicz

[11] Patent Number: 6,136,537
[45] Date of Patent: *Oct. 24, 2000

[54] GENE EXPRESSION ANALYSIS

[76] Inventor: Stephen C. Macevicz, 21890 Rucker Dr., Cupertino, Calif. 95014

[*] Notice: This patent is subject to a terminal disclaimer.

[21] Appl. No.: 09/187,793

[22] Filed: Nov. 6, 1998

Related U.S. Application Data

[63] Continuation-in-part of application No. 09/028,128, Feb. 23, 1998, Pat. No. 6,054,276.

[51] Int. Cl.$^7$ .............................. C12Q 1/68; C12P 19/34; C12N 15/63
[52] U.S. Cl. ........................ 435/6; 435/320.1; 435/91.4; 435/91.51; 435/91.52
[58] Field of Search .......................... 435/6, 320.1, 91.4, 435/91.51, 91.52

[56] References Cited

U.S. PATENT DOCUMENTS

| | | | |
|---|---|---|---|
| 4,293,652 | 10/1981 | Cohen | 435/172 |
| 5,102,785 | 4/1992 | Livak et al. | 435/6 |
| 5,196,328 | 3/1993 | Tartof | 435/172.3 |
| 5,508,169 | 4/1996 | Deugau | 435/6 |
| 5,604,097 | 2/1997 | Brenner | 435/6 |
| 5,658,736 | 8/1997 | Wong | 435/6 |
| 5,667,970 | 9/1997 | Zhang | 435/6 |
| 5,695,937 | 12/1997 | Kinzler | 435/6 |
| 5,710,000 | 1/1998 | Sapolsky | 435/6 |
| 5,728,524 | 3/1998 | Sibson | 435/6 |

FOREIGN PATENT DOCUMENTS

| | | |
|---|---|---|
| 0593095A1 | 4/1994 | European Pat. Off. . |
| 0761822 A2 | 3/1997 | European Pat. Off. . |
| WO 98/10095 | 3/1998 | WIPO . |
| WO 98/31838 | 7/1998 | WIPO . |

OTHER PUBLICATIONS

Chen et al, "Ordered shotgun sequencing, a strategy for integrated mapping and sequencing of YAC clones," Genomics, 17: 651–656 (1993).
Green et al, "Systematic generation of sequence–tagged sites for physical mapping of human chromosomes: application to the mapping of human chromosome 7 using yeast artificial chromosomes," Genomics, 11: 548–564 (1991).
Hudson et al, "An STS–based map of the human genome," Science, 270: 19451954 (1995).
Olson et al, "Random–clone strategy for genomic restriction mapping in yeast," Proc. Natl. Acad. Sci., 83: 7826–7830 (1986).
Michiels et al, "Molecular approaches to genome analysis: a strategy for the construction of ordered overlapping clone libraries," CABIOS, 3: 203–210 (1987).
Poustka and Lehrach, "Jumping libraries and linking libraries: the next generation of molecular tools in mammalian genetics," Trends in Genetics, 2: 174–179 (1986).
Poustka and Lehrach, "Chromosome jumping: a long range cloning technique," in Genetic Engineering: Principles and Methods, J.K. Setlow, Editor, vol. 10, pp. 169–193 (1988).
Evans, "Combinatoric strategies for genome mapping," BioEssays, 13: 39–44 (1991).
Collins et al, "Directional cloning of DNA fragments at a large distance from an initial probe: a circularization method," Proc. Natl. Acad. Sci., 81: 6812–6816 (1984).
Velculescu et al, "Serial analysis of gene expression," Science, 270: 484–487 (1995).
Smith et al, "Genomic sequence sampling: a strategy for high resolution sequence–based physical mapping of complex genomes," Nature Genetics, 7: 40–47 (1994).
Hasan et al, "An Mbo II/Fok I trimming plasmid allowing consecutive cycles of precise 1– to 12– base–pair deletions in cloned DNA," Gene, 82: 305–311 (1989).
Hasan et al, "A novel multistep method for generating precise unidirectional deletions using Bsp MI, a class–IIS restriction enzyme," Gene, 50: 55–62 (1986).
Collins, "Identifying human disease genes by positional cloning," The Harvey Lectures, Series 86, pp. 149–164 (1992).
Collins, "Positional cloning moves from perdition to tradition," Nature Genetics, 9: 347–350 (1995).
Wong et al, "Multiple–complete–digest restriction fragment mapping: Generating sequence–ready maps for large–scale DNA sequencing," Proc. Natl. Acad. Sci., 94: 5225–5230 (1997).
Yi et al, "Construction of restriction fragment maps of 50– to 100–kilobase DNA," Methods in Enzymology, 218: 651–671 (1993).
Smith et al, "A simple method for DNA restriction site mapping," Nucleic Acids Research, 3: 2387–2398 (1976).
Roach et al, "Pairwise end sequencing: A unified approach to genomic mapping and sequencing," Genomics, 26: 345–353 (1995).
Sapolsky et al, "Mapping genomic library clones using oligonucleotide arrays," Genomics, 33: 445–456 (1996).
Kato, "RNA fingerprinting by molecular indexing," Nucleic Acids Research, 24: 394–395 (1996).
Kato, "Description of the entire mRNA population by a 3' end cDNA fragment generated by class IIs restriction enzymes," Nucleic Acids research, 23: 3685–3690 (1995).

*Primary Examiner*—Jeffrey Fredman
*Assistant Examiner*—Juliet C Einsmann

[57] ABSTRACT

The invention provides a method and materials for analyzing the frequency of sequences in a population of polynucleotides, such as a cDNA library. A population of restriction fragments is formed which is inserted into vectors which allow segments to be removed from each end of the inserted fragments. The segments from each restriction fragment are ligated together to form a pair of segments which serves as a tag for the restriction fragment, and the polynucleotide from which the fragment is derived. Pairs of segments are excised from the vectors and ligated to form concatemers which are cloned and sequenced. A tabulation of the sequences of pairs provides a frequency distribution of sequences in the population.

8 Claims, 1 Drawing Sheet

Fig. 1

GENE EXPRESSION ANALYSIS

This is a continuation-in-part application of U.S. patent application Ser. No. 09/028,128 filed Feb. 23, 1998 now U.S. Pat. No. 6,054,276, which is incorporated by reference.

FIELD OF THE INVENTION

The invention relates generally to methods and compositions for quantitative analysis of gene expression, and more particularly, to methods and compositions for accummulating and analyzing sequence tags sampled from a population of expressed genes.

BACKGROUND

The desire to decode the human genome and to understand the genetic basis of disease and a host of other physiological states associated differential gene expression has been a key driving force in the development of improved methods for analyzing and sequencing DNA, Adams et al, Editors, Automated DNA Sequencing and Analysis (Academic Press, New York, 1994). The human genome is estimated to contain about $10^5$ genes, about 15–30% of which—or about 4–8 megabases—are active in any given tissue. Such large numbers of expressed genes make it difficult to track changes in expression patterns by available techniques, such as with hybridization of gene products to microarrays, direct sequence analysis, or the like. More commonly, expression patterns are initially analyzed by lower resolution techniques, such as differential display, indexing, subtraction hybridization, or one of the numerous DNA fingerprinting techniques, e.g. Vos et al, Nucleic Acids Research, 23: 4407–4414 (1995); Hubank et al, Nucleic Acids Research, 22: 5640–5648 (1994); Lingo et al, Science, 257: 967–971 (1992); Erlander et al, International patent application PCT/US94/13041; McClelland et al, U.S. Pat. No. 5,437,975; Unrau et al, Gene, 145: 163–169 (1994); Hubank et al, Nucleic Acids Research, 22: 5640–5648 (1994); Geng et al, BioTechniques, 25: 434–438 (1998); and the like. Higher resolution analysis is then frequently carried out on subsets of cDNA clones identified by the application of such techniques, e.g. Linskens et al, Nucleic Acids Research, 23: 3244–3251 (1995).

Recently, two techniques have been implemented that attempt to provide direct sequence information for analyzing patterns of gene expression. One involves the use of microarrays of oligonucleotides or polynucleotides for capturing complementary polynucleotides from expressed genes, e.g. Schena et al, Science, 270: 467–469 (1995); DeRisi et al, Science, 278: 680–686 (1997); Chee et al, Science, 274: 610–614 (1996); and the other involves the excision and concatenation of short sequence tags from cDNAs, followed by conventional sequencing of the concatenated tags, i.e. serial analysis of gene expression (SAGE), e.g. Velculescu et al, Science, 270: 484–486 (1995); Zhang et al, Science, 276: 1268–1272 (1997); Velculescu et al, Cell, 88: 243–251 (1997). Both techniques have shown promise as potentially robust systems for analyzing gene expression; however, there are still technical issues that need to be addressed for both approaches. For example, in microarray systems, genes to be monitored must be known and isolated beforehand, and with respect to current generation microarrays, the systems lack the complexity to provide a comprehensive analysis of mammalian gene expression, they are not readily re-usable, and they require expensive specialized data collection and analysis systems, although these of course may be used repeatedly. In sequence tag systems, although no special instrumentation is necessary and an extensive installed base of DNA sequencers may be used, the selection of type IIs tag-generating enzymes is limited, and the length (nine nucleotides) of the sequence tag in current protocols severly limits the number of cDNAs that can be uniquely labeled. It can be shown that for organisms expressing large sets of genes, such as mammalian cells, the likelihood of nine-nucleotide tags being distinct for all expressed genes is extremely low, e.g. Feller, An Introduction to Probability Theory and Its Applications, Second Edition, Vol. I (John Wiley & Sons, New York, 1971).

It is clear from the above that there is a need for a technique to analyze gene expression that allows both the analysis of unknown genes and the unequivocal assignment of a sequence tag to an expressed gene. The availability of such techniques would find immediate application in medical and scientific research, drug discovery, and genetic analysis in a host of applied fields, such as pest management and crop and livestock development.

SUMMARY OF THE INVENTION

In view of the above, objects of the present invention include, but are not limited to, providing a method for analyzing gene expression by tabulating sequence tags from expressed genes; providing a method of analyzing the expression of genes for which no previous sequence information exists; providing a method of recovering full length sequences of genes that display expression patterns of interest; providing a method of acquiring sequence tags of sufficient length for unequivocal identification of expressed genes; providing a method of measuring sequence frequencies in a population of polynucleotides; providing a method of genetic identification by tabulations of genomic sequence tags; and providing compositions and kits for implementing the method of the invention.

The invention achieves these and other objects by providing methods and materials for acquiring sequence tags from a population of polynucleotides, such as a cDNA or genomic library, or a sample thereof. In accordance with the invention, the nucleotide sequence of a portion of each end of each polynucleotide of the population is determined so that a pair of nucleotide sequences, or sequence tags, is obtained for each polynucleotide. Preferably, the method of the invention comprises the steps of i) providing a population of polynucleotides having predetermined ends; ii) inserting each polynucleotide of the population into a vector, so that the vector has at least one type IIs restriction endonuclease recognition site adjacent to each end of the inserted polynucleotide, each type IIs restriction endonuclease recognition site being oriented such that a type IIs restriction endonuclease recognizing either site cleaves the vector interior to the inserted polynucleotide; iii) cleaving each vector with one or more type IIs restriction endonucleases recognizing the type IIs restriction endonuclease recognition sites so that the vector is linearized and has a sequence tag of the inserted polynucleotide at each end; iv) re-circularizing the vector to form a pair of sequence tags for the inserted polynucleotide; and v) determining the nucleotide sequence of each pair of sequence tags of a sample of re-circularized vectors. Preferably, the population of polynucleotides having predetermined ends is produced by digesting a cDNA library with one or more frequent-cutting restriction endonucleases, e.g. restriction endonucleases each having a four-base recognition sequences. Preferably, the pairs of sequence tags are tabulated to form a frequency distribution of sequences in the population of polynucleotides which may be used directly, or related to the frequency distribution of sequences in another population, such as a cDNA library, from which the analyzed population is derived. In one aspect of the invention, the pairs of sequence tags are excised from the re-circularized vectors and ligated together to form a concatemers, which are cloned in a conventional sequencing vector.

The invention includes compositions and kits for implementing the method of the invention. Preferably, compositions of the invention include vectors for cleaving sequence tags from each end of an inserted polynucleotide, such as that illustrated in FIG. 1. Preferably, kits of the invention include a vector, together with appropriate buffers, restriction endonucleases, and the like, for carrying out the method of the invention.

The present invention provides a means for analyzing gene expression by tabulating pairs of sequence tags from gene expression products, such as cDNAs. The invention provides several advantages over prior art methods of gene expression analysis, including the analysis of unknown genes, longer sequence tags for unequivocal gene identification, more flexibility in the selection of type IIs restriction endonucleases for tag generation, means of retrieving sequences of interest, no specialized instrumentation required for practicing the invention, the existing and projected installed bases of DNA sequencers may be used with the invention, and the like.

DEFINITIONS

The term "oligonucleotide" as used herein includes linear oligomers of natural or modified monomers or linkages, including deoxyribonucleosides, ribonucleosides, and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 34, to several tens of monomeric units, e.g. 40–60. Whenever an oligonucleotide is represented by a sequence of letters (upper case or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Usually oligonucleotides comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

As used herein, the term "complexity" in reference to a population of polynucleotides means the number of different species of polynucleotide present in the population.

As used herein, "amplicon" means the product of an amplification reaction. That is, it is a population of polynucleotides, usually double stranded, that are replicated from one or more starting sequences. The one or more starting sequences may be one or more copies of the same sequence, or it may be a mixture of different sequences. Preferably, amplicons are produced either in a polymerase chain reaction (PCR) or by replication in a cloning vector.

DETAILED DESCRIPTION OF THE INVENTION

Methods and materials are provided for analyzing gene expression by tabulating sequence information from expressed genes. Polynucleotide products of expressed genes are preferably digested with one or more restriction endonucleases to produce a population of fragments with predetermined ends. Preferably, such polynucleotide products, which are usually cDNAs, are digested with one or more "frequent cutting" restriction endonucleases, so that fragments are formed having average lengths in the range of from a few tens of basepairs, e.g. 40–50, to a few hundreds of basepairs, e.g. 200–500, thereby assuring with high probability, e.g. >95%, and more preferably >98%, that every polynucleotide product will be cleaved at least once. Most preferably, frequent cutting restriction endonucleases consist of one or more restriction endonucleases having four-base recognition sites. Exemplary frequent cutting restriction endonucleases for use with the invention include Tsp 509 I, Nla III, Mbo I, Sau 3A I, Dpn II, Aci I, Hpa II, Msp I, Bfa I, HinP1 I, Hha I, Mse I, Taq I, and the like. Preferably, frequent cutting restriction endonucleases are used which produce four-base overhangs, or protruding strands, such as Tsp 509 I, Nla III, Sau 3A, or the like.

Depending on the embodiment, a randomly selected cDNA may be represented by zero, one, or multiple pairs of sequence tags. If no linkers are added during cDNA library construction that contain restriction sites (described more fully below), no pairs of sequence tags will be obtained if the cDNA is cleaved only once or not at all by the one or more restriction enzymes used; a single pair of sequence tags will be obtained if two cleavage sites are present; and n−1 pairs of sequence tags will be obtained if n cleavage sites are present. In the preferred embodiment where linkers are added, these numbers become one, two, or multiple pairs of sequence tags, respectively. Consequently, a frequency distribution of pairs of sequence tags taken from a cDNA library will usually not reflect the actual frequencies of the mRNAs from which the library was derived. However, the observed frequencies of pairs of sequence tags will be simple integral multiples of the actual frequencies; thus, changes in the relative frequencies of expressed sequences between two or more populations, e.g. cDNA libraries taken under different conditions, are readily observable. Moreover, multiple pairs of sequence tags per expressed gene also provide an internal control for tracking changes in frequencies, particularly for genes whose sequences are already known. If the frequency of an expressed gene doubles, then the frequency of each pair of its sequence tags should also double. The following table provides guidance regarding the changes in observed expression frequencies to be expected with application of the method of the invention:

Expected Number of Fragments (without Linkers)

| Length of cDNA (basepairs) | Probability of at least 2 restriction sites of one 4-cutter | Expected number of restriction fragments per cDNA | Probability of at least 2 restriction sites of two 4-cutters | Expected number of restriction fragments per cDNA |
|---|---|---|---|---|
| 500 | .58 | 1.95 | .90 | 3.9 |
| 1000 | .90 | 3.9 | .996 | 7.8 |
| 1500 | .98 | 5.9 | .999 | 11.7 |
| 2000 | .996 | 7.8 | .999 | 15.6 |

Thus, if a gene expression profile consisted of the expression four cDNAs 500, 1000, 1500, and 2000 basepairs in length in a proportion of 1:1:1:1, the observed profile under the method of the invention would be about 1:2:3:4, assuming that an adequate sample of pairs of sequence tag is taken, that the sequences of the expressed genes are known, and that fragments are generated by cleavage with a single four-base cutter. The latter ratio results because in a random sample of pairs of sequence tags, one would be four times more likely to select a pair from the 2000 basepair cDNA as from the 500 basepair cDNA, three times more likely to select a pair from the 1500 basepair cDNA as from the 500 basepair cDNA, and so on. If under different conditions the expression of the 1000 basepair cDNA doubled resulting in an expression profile of 1:2:1:1, then the profile observed by application of the invention would be 1:4:3:4. If, for example, the sequence of the 500 basepair cDNA were unknown, so that there was no way to know that the fragments generated in the method of the invention were from the same gene, then the observed fragments generated in the method of the invention were from the same gene, then the observed expression profile would be more complex. If two fragments were generated from the 500 basepair cDNA, then an expression profile would consist of a ratio of five numbers: 1:1:4:6:8. Likewise, if the 2000 basepair cDNA was from an unknown gene and eight fragments were generated by the method, then the observed expression profile would correspond to the ratio 1:1:1:1:1:1:1:2:4:6.

Pairs of sequence tags may be obtained from cDNAs without cleavage by a restriction endonuclease; however, one of the sequence tags of each pair in such embodiments typically consists of a segment of the polyA tail of the cDNA and therefore lacks information content. The number of such pairs of sequence tags provides an estimate of the total number of expressed sequences obtained in a sample.

Preferably, the efficiency of detecting expressed genes is increase by employing linkers ligated to the ends of the cDNAs after second strand synthesis. Conventional protocols may be followed, e.g. Section III, Ausubel et al, editors, Current Protocols in Molecular Biology (John Wiley & Sons, New York, 1997); however, the usual methylation step of such conventional protocols is omitted. Preferably, the restriction site contained in a linkers is recognized by at least one of the restriction endonucleases used to generate the polynucleotides with predetermined ends. Thus, every cDNA will always give rise to at least one fragment. With linkers, the expected number of fragments per cDNA increases as follows:

Expected Number of Fragments (with Linkers)

| Length of cDNA (basepairs) | Probability of at least 1 internal restriction site of single 4-cutter (i.e. equals the probability of there being at least two fragments) | Expected Number of restriction fragments per cDNA | Probability of at least 1 internal restriction sites of two 4-cutters (i.e. equals the probability of there being at least two fragments) | Expected Number of restriction fragments per cDNA |
|---|---|---|---|---|
| 500 | .857 | 2.95 | .90 | 4.9 |
| 1000 | .980 | 4.9 | .996 | 8.8 |
| 1500 | .997 | 5.9 | .999 | 12.7 |
| 2000 | .999 | 8.8 | .999 | 16.6 |

Figure 1:
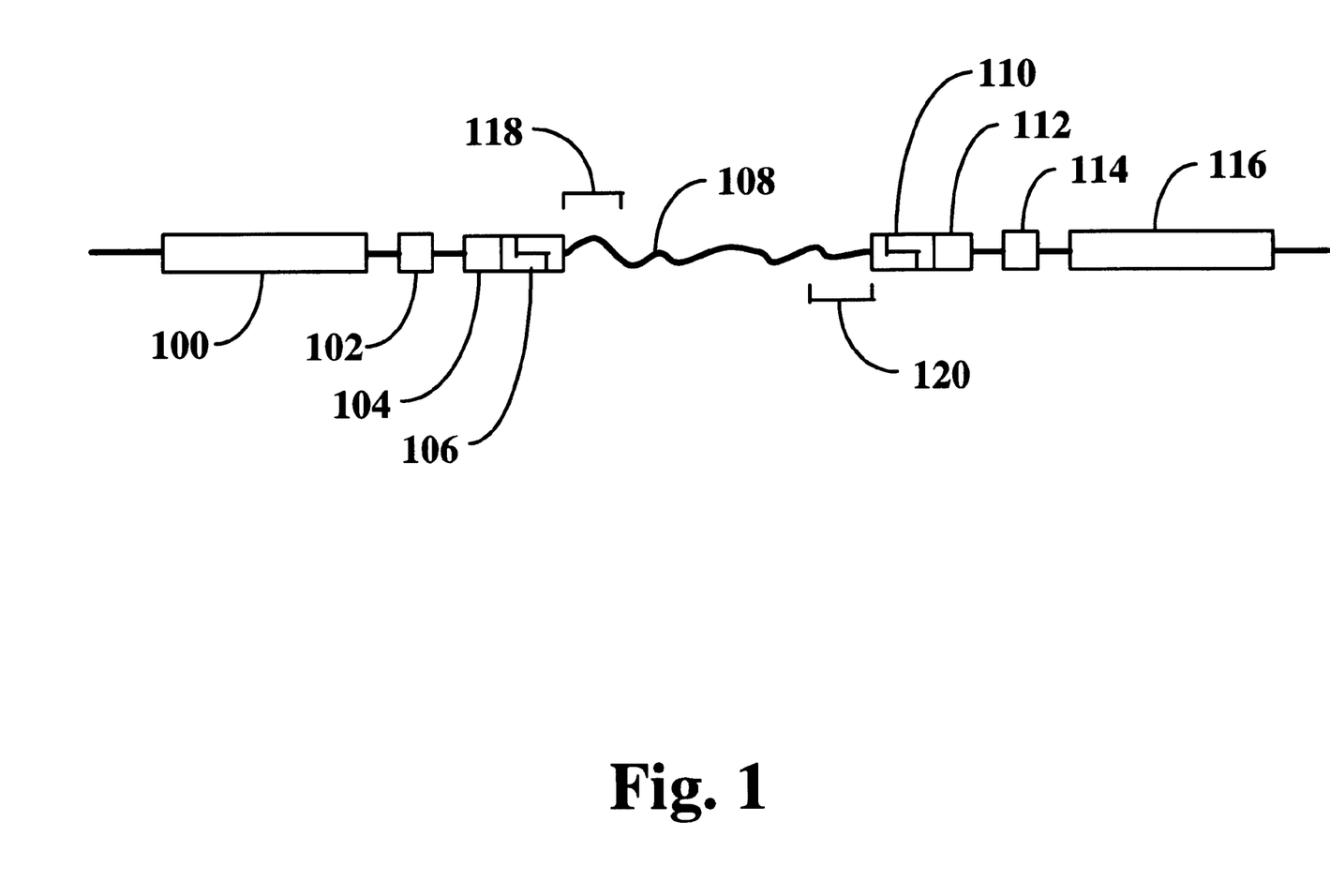
FIG. 1 contains a diagram of a vector for forming pairs of nucleotide sequences in accordance with a preferred embodiment of the invention.

Preferably, the method of the invention is carried out using a vector, such as that illustrated in FIG. 1. The vector is readily constructed from commercially available materials using conventional recombinant DNA techniques, e.g. as disclosed in Sambrook et al, Molecular Cloning, Second Edition (Cold Spring Harbor Laboratory, New York, 1989). Preferably, pUC-based plasmids, such as pUC 19, or Abased phages, such as λZAP Express (Stratagene Cloning Systems, La Jolla, Calif.), pZErO (Invitrogen Corp., Carlsbad, Calif.), or like vectors are employed. Important features of the vector are recognition sites (104) and (112) for two type Us restriction endonucleases that flank restriction fragment (108). For convenience, the two type IIs restriction enzymes are referred to herein as "$IIs_1$" and "$IIs_2$", respectively. IIs, and Its$_2$ may be the same or differ ent. Recognition sites (104) and (112) are oriented so that the cleavage sites of $IIs_1$ and $IIs_2$ are located in the interior of restriction fragment (108). In other words, taking the 5' direction as "upstream" and the 3' direction as "downstream," the cleavage site of $IIs_1$ is downstream of its recognition site and the cleavage site of $IIs_2$ is upstream of its recognition site. Thus, when the vector is cleaved with $IIs_1$ and $IIs_2$, two segments (118) and (120) of restriction fragment (108) remain attached to the vector. The vector is then re-circularized by ligating the two ends together, thereby forming a pair of segments, or sequence tags. If such cleavage results in one or more single stranded overhangs, i.e. one or more non-blunt ends, then the ends are preferably rendered blunt prior to re-circularization, for example, by digesting the protruding strand with a nuclease such as Mung bean nuclease, T4 DNA polymerase, or the like, or by extending a 3' recessed strand, if one is produced in the digestion, or by providing an adaptor mixture. The ligation reaction for re-circularization is carried out under conditions that favor the formation of covalent circles rather than concatemers of the vector. Preferably, the vector concentration for the ligation is between about 0.4 and about 4.0 μg/ml of vector DNA, e.g. as disclosed in Collins et al, Proc. Natl. Acad. Sci., 81: 6812–6812 (1984), for λ-based vectors. For vectors of different molecular weight, the concentration range is adjusted appropriately, e.g. Dugaizxyk et al, J. Mol. Biol., 96: 171–184 (1975).

In the preferred embodiments, the number of nucleotides identified depends on the "reach" of the type IIs restriction endonucleases employed. "Reach" is the amount of separation between a recognition site of a type Us restriction endonuclease and its cleavage site, e.g. Brenner, U.S. Pat. No. 5,559,675. The conventional measure of reach is given as a ratio of integers, such as "(16/14)", where the numerator is the number of nucleotides from the recognition site in the 5'→3' direction that cleavage of one strand occurs and the denominator is the number of nucleotides from the recognition site in the 3'→5' direction that cleavage of the other strand occurs. Preferred type IIs restriction endonucleases for use as $IIs_1$ and $IIs_2$ in the preferred embodiment include the following: Bbv 1, Bce 83 I, Bcef 1, Bpm I, Bsg I, BspLU 11 III, Bst 71 I, Eco 57 I, Fok I, Gsu I, Hga I, Mme I, and the like. In the preferred embodiment, a vector is selected which does not contain a recognition site, other than (104) and (112), for the type IIs enzyme(s) used to generate pairs of segments; otherwise, re-circularization cannot be carried out. Preferably, a type IIs restriction endonuclease for generating pairs of segments has as great a reach as possible to maximize the probability that the nucleotide sequences of the segments are unique.

Immediately adjacent to Us sites (104) and (112) are restriction sites (106) and (1 10), respectively that permit restriction fragment (108) to be inserted into the vector. That is, restriction site (106) is immediately downstream of (104) and (110) is immediately upstream of (112). Preferably, sites (104) and (106) are as close together as possible, even overlapping, provided type IIs site (106) is not destroyed upon cleavage with the enzymes for inserting restriction fragment (108). This is desirable because the recognition site of the restriction endonuclease used for generating the fragments occurs between the recognition site and cleavage site of type IIs enzyme used to remove a segment for sequencing, i.e. it occurs within the "reach" of the type IIs enzyme. Thus, the closer the recognition sites, the larger the piece of unique sequence can be removed from the fragment. The same of course holds for restriction sites (110) and (112). Preferably, whenever the vector employed is based on a pUC plasmid, restriction sites (106) and (110) are selected from restriction sites of polylinker region of the pUC plasmid that upon cleavage leave ends compatible with ends left by the frequent cutting enzyme being employed. For example, Tsp 509 fragments may be inserted into an Eco RI site, Nla III fragments may be inserted into Sph I or Nsp I sites, and Sau 3A fragments may be inserted into Bam HI, Bcl I, Bgl II, or Bst YI sites.

Preferably, the vectors contain primer binding sites (100) and (116) for primers $p_1$ and $p_2$, respectively, which may be used to amplify the pair of segments by PCR after re-circularization. Recognition sites (102) and (114) are for restriction endonucleases $w_1$ and $w_2$, which are used to cleave the pair of segments from the vector after amplification. Preferably, $w_1$ and $w_2$, which may be the same or different, are type Us restriction endonucleases whose cleavage sites correspond to those of (106) and (1 10), thereby removing surplus, or non-informative, sequence (such as the recognition sites (104) and (112)) and generating protruding ends that permit concatenation of the pairs of segments.

As mentioned above, preferably polynucleotides for analysis by the method of the invention are derived from mRNA extracted from a cell or tissue source. mRNA may be prepared by a commercially available mRNA extraction kit using conventional protocols, e.g. PolyATract series 9600 kit (Promega, Madison, Wis.); FastTrack 2.0 kit (Invitrogen, Calif.); Dynabeads Oligo$(dT)_{25}$ (Dynal, Oslo, Norway), or the like. After extraction, mRNA is converted into cDNA using conventional protocols with minor modifications, such as omission of methylation steps to ensure that the cDNA can be cleaved with selected restriction endonucleases. Again, cDNA synthesis may be accomplished using commercially available kits, e.g. StrataScript RT-PCR kit (Stratagene Cloning Systems, La Jolla, Calif.); SMART PCR cDNA Synthesis kit (Clontech Laboratories, Palo Alto, Calif.); Riboclone cDNA Synthesis System (Promega Corp., Madison, Wis.); or the like. Preferably, a protocol is employed which results in the conversion of mRNA into blunt-ended double-stranded cDNA, after which linkers, each containing a selected restriction site, are ligated to the cDNA. The selected restriction site preferably corresponds to that of, or includes a site of, one of the one or more restriction endonucleases used to generate a population of polynucleotides, e.g. cDNA fragments, with predetermined ends. Alternatively, a biotinylated oligo-dT primer is provided for first strand synthesis which results in the production of cDNAs having a biotin group that permits purification on a conventional avidinated solid phase support, e.g. M-280 Dynabeads (Dynal, Oslo, Norway). Preferably, linkers containing a recognition site of the selected four-base cutter are ligated to the opposite ends of the cDNAs. After affinity purification, the cDNAs may be digested with a selected four-base cutting endonuclease and the released fragments used for analysis in accordance with the invention.

In some applications of the invention, it may be desirable to employ a cDNA construction technique that maximizes the production of full length cDNAs. In this way, cDNAs that are randomly truncated near their 5' ends are minimized and a source of noise in the gene expression measurements is reduced or eliminated. Techniques for full length cDNA production are disclosed in Carninci et al, DNA Research, 4: 61–66 (1997); and CapFinder PCR cDNA Synthesis kit product literature (Clontech Laboratories, Palo Alto, Calif.). Alternatively, 3' biases in clone representation can be reduced by using a random priming technique for first strand synthesis of cDNAs, e.g. Koike et al, Nucleic Acids Research, 15: 2499 (1987). Random-primer kits are commercially available, e.g. RiboClone cDNA Synthesis System (Promega Corp., Madison, Wis.); or the like.

After insertion of the fragments into a vector, a suitable host is transformed with copies of the vector and cultured, i.e. expanded, using conventional techniques. Transformed host cells are then selected, e.g. by plating and picking colonies using a standard marker, e.g. β-glactosidase/X-gal. Alternatively, the fragments may be cloned into a vector which forces selection against non-recombinants, e.g. pZErO series of vectors available from Invitrogen Corp. (Carlsbad, Calif.). A large enough sample of recombinant-containing host cells is taken to ensure that at least one pair from every fragment is present for analysis with a reasonably large probability. The number of fragments, N, that must be in a sample to achieve a given probability, P, of including a given fragment is the following: N=1n(1−P)/1n (1−f), where f is the frequency of the fragment in the population. Thus, for a population of 10,000 different kinds of cDNA, a sample containing 69,000 vectors will include at least one copy of each fragment (even those present at a frequency of 1 in 10,000) with a probability of 99.9%; and a sample containing 46,000 vectors will include at least one copy of each fragment with a probability of 99%. For this calculation, it is assumed that each cDNA is cleaved into the same number of fragments. By varying the number of pairs sequenced, the sensitivity of the technique for detecting changes in expression can also be varied. Preferably, a sample size is employed that results in a least one copy of every sequence present at a frequency of 0.1 percent in the population being studied with a probability of 99%. More preferably, a sample size is employed that results in a least one copy of every sequence present at a frequency of 0.01 percent in the population being studied with a probability of 99%.

After selection, the vector-containing hosts are combined and expanded in cultured. The vectors are then isolated, e.g. by a conventional mini-prep, or the like, and cleaved with $IIs_1$ and $IIs_2$. The fragments comprising the vector and ends (i.e. segments) of the restriction fragment insert are isolated, e.g. by gel electrophoresis, blunted, and re-circularized. The resulting pairs of segments in the re-circularized vectors are then amplified, e.g. by polymerase chain reaction (PCR), after which the amplified pairs are cleaved with w to free the pairs of sequence tags, which are then isolated, e.g. by gel electrophoresis, or like technique. Preferably, the isolated pairs are concatenated in a conventional ligation reaction to produce concatemers of various sizes, which are separated, e.g. by gel electrophoresis. Concatemers greater than about 200–300 basepairs are isolated and cloned into a standard sequencing vector, such as pUC 19, pBluescript, M13, or the like. The sequences of the cloned concatenated pairs are analyzed on a conventional DNA sequencer, such as a model 377 DNA sequencer from Perkin-Elmer Applied Biosystems Division (Foster City, Calif.).

In the above embodiment, the sequences of the pairs of segments are readily identified between sequences for the recognition site of the enzymes used in the digestions. For example, when pairs are concatenated from fragments produced by digestion with frequent cutting enzyme r and cleavage with a type IIs restriction endonuclease of reach (16/14), the following pattern is observed:

NNNNrrrrNNNNNNNNNNNNNNNNNNNNNrrrrNNNNNN where "r" represents the nucleotides of the recognition sites of restriction endonuclease r, and where the N's are the nucleotides of the pairs of sequence tags. Thus, the pairs are recognized by their length and their spacing between known recognition sites, and in this embodiment, each pair of sequence tags requires that a sequence of 22 nucleotide be identified. Assuming that 20 pairs, or 440 bases, are sequenced in each sequencing reaction in a conventional sequencing protocol, about 2300 sequencing reactions must be carried out and the same number of electrophoretic separations must be made to analyzed 46,000 pairs of sequence tags.

As mentioned above, multiple frequent cutting restriction endonucleases may be employed in which case multiple cloning vectors or adaptors must be used for capturing all fragment types. For example, is if two frequent cutters r and q are used, three fragment types are produced: those with both ends resulting from cleavage by r, or r-r fragments; those with both ends resulting from cleavage by q, or q-q fragments; and those with mixed ends, or r-q fragments. Linkers may also be employed in such multiple enzyme embodiments. A single cloning vector may be used if adaptors are provided to convert the ends of the various fragment types to ends that allow insertion into the cloning vector. Preferably, in such embodiments, the adaptors include a recognition site for the type IIs restriction endonuclease used to generate sequence tags. For example, if Tsp 509 and Sau 3A are used to generate fragments from a cDNA library and if Bsg I is the type IIs restriction endonuclease used to generate sequence tags, such adaptors can have the following form (SEQ ID NO: 1, SEQ ID NO: 2, and SEQ ID NO: 3) for insertion into an Eco RI site of a cloning vector:

Thus, after a cDNA library is digested to completion with Tsp 509 and Sau 3A, the above adaptors are ligated to the ends of the fragments followed by digestion with Eco RI. The fragments are then treated as described above in the single frequent cutter embodiment.

The following examples serve to illustrate the present invention and are not meant to be limiting. Selection of many of the reagents, e.g. enzymes, vectors, and other materials; selection of reaction conditions and protocols; and material specifications, and the like, are matters of design choice which may be made by one of ordinary skill in the art. Extensive guidance is available in the literature for applying particular protocols for a wide variety of design choices made in accordance with the invention, e.g. Sambrook et al, Molecular Cloning, Second Edition (Cold Spring Harbor Laboratory, New York, 1989); Ausubel et al, editors, Current Protocols in Molecular Biology (John Wiley & Sons, New York, 1997); and the like.

EXAMPLE 1

Analysis of Yeast Gene Expression by Tsp 509 Digestion of a cDNA Library having Eco RI Linkers In this example, a cDNA library is constructed from mRNA extracted from *Saccharomyces cerevisiae* cells of strain YPH499 (ATCC accession No. 76625). After ligation of commercial Eco RI linkers, the cDNAs are digested to completion with four-base cutter, Tsp 509 I, and are inserted into a pUC 19 cloning vector modified as described below for explansion and generation of pairs of sequence tags. The pairs of sequence tags are excised from the vector, ligated to form concatemers, cloned, and sequenced.

Synthetic oligonucleotides (i) through (iv) are combined with an Eco RI and Hind III digested pUC 19 in a conventional ligation reaction so that they assemble into the double stranded insert of Formula II:

(i)   5'-aattagccgtacctgcagcagtgcagg         (SEQ ID NO: 4)

(ii)  5'-p-aattcctgcacagctgcgaatcattcg       (SEQ ID NO: 5)

(iii) 5'-agctcgaatgattcgcagctgt              (SEQ ID NO: 6)

(iv)  5'-p-gcaggaattcctgcactgctgcaggtacggct  (SEQ ID NO: 7)

where the 5' "p's" in formulas (ii) and (iv) represent 5' phosphate groups.

Formula II (SEQ ID NO:8)

```
              →        →
            Bbv I    Bsg I
              ↓        ↓
5'-AATTAGCCGTACCTGCAGCAGTGCAG-

TCGGCATGGACGTCGTCACGTC-

-GAATTCCTGCACAGCTGCGAATCATTCG

-CTTAAGGACGTGTCGACGCTTAGTAAGCTCGA
           ↑            ↑         ↑
         Eco RI       Bsg I     Bbv I
                        ←         ←
```

Note that the insert has compatible ends to the Eco RI-Hind III-digested plasmid, but that the original Eco RI and Hind III sites are destroyed upon ligation. The horizontal arrows above and below the Bsg I and Bbv I sites indicate the direction of the cleavage site relative to the recognition site of the enzymes. After ligation, transformation of a suitable host, and expansion, the modified pUC 19 is isolated and the insert is sequenced to confirm its identity.

Yeast cells are grown at 30° C. in YPD rich medium, YPD supplemented with 6 mM uracil, 4.8 mM adenine, and 24 mM tryptophan)(Rose et al, Methods in Yeast Genetics (Cold Spring Harbor Laboratory Press, 1990)). Cell density is measured by counting cells from duplicate dilutions, and the number of viable cells per milliliter is estimated by plating dilutions of the cultures on YPD agar immediately before collecting cells for mRNA extraction. Cells is mid-log phase ($1-5 \times 10^7$ cells/ml) are pelleted, washed twice with AE buffer solution (50 mM NaAc, pH 5.2, 10 mM EDTA), frozen in a dry ice-ethanol bath, and stored at −80° C.

Total RNA is extracted from frozen cell pellets using a hot phenol method, described by Schmitt et al, Nucleic Acids Research, 18: 3091–3092 (1990), with the addition of a chloroform-isoamyl alcohol extraction just before precipitation of the total RNA. Phase-Lock Gel (5 Prime-3 Prime, Inc., Boulder, Colo.) is used for all organic extractions to increase RNA recovery and decrease the potential for contamination of the RNA with material from the organic interface. Poly(A)$^+$ RNA is purified from the total RNA with an oligo-dT selection step (Oligotex, Qiagen, Chatsworth, Calif.).

10 μg mRNA from the yeast cells is reverse transcribed with a commercially available kit (e.g., RiboClone cDNA Synthesis System, Promega Corp., Wis.) which follows the protocol described in Ausubel et al (cited above), pages 5.5.1–5.5.13 and 5.6.1–5.6.10. Briefly, 10 μg mRNA at a concentration of 1 μg/μl is heated in a tightly sealed microcentrifuge tube for 5 min at 65° C., then placed immediately on ice. In a separate tube, the following components are added in the following order to give a total volume of about 180 μl: 20 μl 5 mM dNTPs (each at 500 μM final concentration); 40 μl 5× RT buffer (for a final concentration of 1×); 10 μl 200 mM dithiothreitol (10 mM final concentration); 20 μl 0.5 mg/ml oligo(dT)$_{12-18}$ (50 μg/ml final concentration); 60 μl H$_2$O; and 10 μl (10 units) RNasin (50 units/ml final concentration). 5× RT buffer is 250 μl 1M Tris-Cl (pH 8.2); 250 μl 1M KCl; 30 μl 1M MgCl$_2$; and 470 μl H$_2$O. The components are mixed by vortexing, briefly microcentrifuged, and then added to the tube containing the RNA, after which 20 μl AMV reverse transcriptase (200 units) is added for a final concentration of 1000 units/ml in 200 μl. After mixing by vortexing, 10 μl of the mixture is removed to a separate tube containing 1 μl of [α-$^{32}$P]dCTP, after which both tubes are incubated at room temperature for 5 min, then at 42° C. for 1.5 hours. After 1.5 hours, 1 μl of 0.5M EDTA (pH 8.0) is added to the tube with the radioactive label to quench the reaction. This sample is used to estimate the amount of cDNA synthesized in the reaction. To the main reaction, 4 μl of 0.5M EDTA (pH 8.0) and 200 μl buffered phenol is added. After vortexing, the mixture is microfuged at room temperature for 1 min to separate the phases, after which the upper aqueous phase is transferred to a new tube. To the phenol layer, add 100 μl TE buffer (pH 7.5), vortex, and microcentrifuge as described above. Remove the aqueous layer and add it to the aqueous phase from the first extraction. To the aqueous solution, add 1 ml diethyl ether, vortex, and microcentrifuge as described above, after which the upper (ether) layer is removed with a glass pipet and discarded. Repeat the extraction with an additional 1 μl diethyl ether. Add 125 μl of 7.5M ammonium acetate to the aqueous phase (to give a final concentration of about 2.0–2.5M) and 950 μl of 95% ethanol. Place in dry ice/ethanol bath 15 min, warm to 4° C., and microcentrifuge at 4° C. for 10 min at full speed to pellet the nucleic acids, which may be visible as a small yellow-white pellet. After removing the supernatant with a pipet, fill the tube with ice-cold 70% ethanol, and microcentrifuge at 4° C. for 3 min at full speed. Remove the supernatant and dry the tube containing the precipitated DNA in a vacuum desiccator. Resuspend the pellet from the first-strand synthesis in 284 μl water and add to the tube the following components in the following order to give a final volume of 400 μl; 4 μl 5 mM dNTPs (50 μM final concentration each); 80 μl 5× second-strand buffer (to give a 1× final concentration); 12 μl 5 mM β-AND$^+$ (150 μM final concentration); and 2 μl 10 μCi/μl [α-$^{32}$P]dCTP (50 μCi/ml final) to monitor nucleotide incorporation. 5× second-strand buffer is 100 μl 1 M Tris-Cl (pH 7.5), 500 μl 1M KCl, 25 μl 1M MgCl$_2$, 50 μl 1M (NH$_4$)$_2$SO$_4$, 50 μl 1M dithiothreitol, 50 μl 5 mg/ml bovine serum albumin, and 225 Ill H$_2$0. After vortexing, briefly microcentrifuge, then add the following: 4 μl (4 units) RNase H (10 units/ml final concentration); 4 μl (20 units) *E. coli* DNA ligase (50 units/ml final); and 10 μl (100 units) *E. coli* DNA polymerase I (250 units/ml final). After vortexing and briefly microcentrifuging, the mixture is incubated at 14° C. for 12 to 16 hours. After second strand synthesis is complete, phenol extract the reaction mixture with 400 μl buffered phenol and remove the aqueous phase. Back extract the phenol phase with 200 μl TE (pH 7.5) as described above. Pool the aqueous phases and extract twice with 900 μl ether, as described above, to give a final aqueous phase of about 600 μl. Divide the aqueous phase evenly between two tubes, add ammonium acetate, and ethanol precipitate, as described above. Second strand synthesis is completed and the ends of the cDNA blunted as follows: Resuspend the pooled pellets in 42 μl water and add the following components in the following order to give a final volume of 80 μl: 5 μl 5 mM dNTPs (310 μM final concentration each); 16 μl 5× TA buffer (1× final concentration); and 1 μl 5 mM β-NAD+ (62 μM final concentration). 5× TA buffer is 200 μl 1M Tris-acetate (pH 7.8); 400 μl 1M potassium acetate, 60 μl 1M magnesium acetate, 3 μl 1M dithiothreitol, 105 μl 5 mg/ml bovine serum albumin, and 432 μl $H_2O$. After vortexing and briefly microcentrifuging, the following are added: 4 μl of 2 μg/ml RNase A (100 ng/ml final concentration); 4 μl (4 units) RNase H (50 units/ml final); 4 μl (20 units) *E. coli* DNA ligase (250 units/ml final); and 4 μl (8 units) T4 DNA polymerase (100 units/ml final). The mixture is vortexed, briefly microcentrifuged, and incubated 45 min at 37° C., after which 120 μl TE (pH 7.5) and 1 μl of 10 mg/ml tRNA is added. The resulting mixture is extracted with 200 μl buffered phenol. After removal of the aqueous phase, the phenol phase is back extracted with 100 μl TE as described above. The two aqueous phases are pooled and extracted twice with 1 ml ether, as described above, after which the cDNA is ethanol precipitated as described above.

Eco RI linkers (New England Biolabs, Beverly, Mass.) are ligated to the ends of the cDNAs in a conventional ligation reaction: cDNA from the above reaction is disolve in 23 μl water, after which the following components are added in the following order: 3 μl 10× T4 DNA ligase buffer (manufacturer's recommendation) containing 5 mM ATP (to 1× final buffer concentration and 0.5 mM final ATP concentration), and 2 μl 1 μg/l phosphorylated Eco RI linkers (67 μg/ml final concentration) to give a final volume of 30 μl. After gentle mixing, 2 μl (800 units) T4 DNA ligase (New England Biolabs) is added (27,000 units/ml final) and the mixture is incubated overnight at 4° C. After microcentrifuging briefly, the ligase is inactivated by heating the reaction mixture to 65° C. for 10 min in a water bath, after which the mixture is placed on ice for 2 min. To the reaction mixture, the following components are added in the following order: 95 μl $H_2O$ and 15 μl 10× Eco RI buffer (1× final concentration). After gentle mixing, 10 μl (200 units) Eco RI is added to give a final concentration of 1300 units/ml and the mixture is incubated for 4 hours at 37° C. After such incubation, an additional 3 μl (60 units) of Eco RI is added to the mixture, after which it is gently mixed and incubated another hour at 37° C. to ensure complete digestion of the cDNA and linkers. The restriction fragments are separated from the rest of the reaction mixture by CL-4B column chromatography, e.g. as taught by Ausebel et al, unit 5.6 Current Protocols (cited above). Alternatively, fragments may be purified by passing the reaction mixture through a conventional spin column, such as a Chroma Spin-30 column (Clontech Laboratories, Palo Alto, Calif.), or the like.

As another alternative, ethidium-labeled fragments may be purified by agarose gel electrophoresis, followed by excision of the fragment-containing portion of the gel and dialysis. After purification, the fragments are ethanol precipitated.

1 μg (0.57 pmol) of the above-modified pUC 19 plasmid is digested with Eco RI in Eco RI buffer as recommended by the manufacturer (New England Biolabs, Beverly, Mass.), purified by phenol extraction and ethanol precipitation, and ligated to a two molar excess of fragments (about 200 ng) in a conventional ligation reaction. A bacterial host is transformed, e.g. by electroporation, and plated so that hosts containing recombinant plasmids are identified by white colonies. 25,000 colonies are picked and expanded in liquid culture.

Plasmid DNA is isolated by conventional alkaline lysis followed by anion-exchange purification using a Qiagen-tip 20 plasmid purification kit (Santa Clarita, Calif.), or like kit. 1 μg of purified plasmid DNA is digested to completion with Bsg I using the manufacturer's protocol (New England Biolabs, Beverly, Mass.), and after phenol extraction, the vector-containing fragment is separated by agarose gel electrophoresis followed by isolation with a QIAquick Gel Extraction Kit (Qiagen, Inc., Santa Clarita, Calif.). The ends of the isolated fragment are then blunted by Mung bean nuclease (using the manufacturer's recommended protocol, New England Biolabs), after which the blunted fragments are purified by phenol extraction and ethanol precipitation. The fragments are then resuspended in a ligation buffer at a concentration of about 1 μg/ml in a 0.5 ml reaction volume. The dilution is designed to promote self-ligation of the fragments, following the protocol of Dugaiczyk et al (cited above). After ligation and concentration by ethanol precipitation, the pairs of segments carried by the plasmids are amplified by PCR using primers $p_1$ and $p_2$. Preferably, $p_1$ and $p_2$ are selected to bind to regions of the vector 5' and 3' of the polylinker site, respectively, so that amplification results in a amplicon of about 110–150 basepairs. 18-mer primers are employed with the 5' most nucleotide of $p_1$ binding to a complementary nucleotide 64 bases upstream of the Eco RI insertion site and the 5' most nucleotide of $p_2$ binding to a complementary nucleotide 36 bases downstream of the Eco RI insertion site. In this manner, three readily readily separatable fragments are product upon digestion with $w_1$ and $w_2$. 15–20 amplification cycles are carried out so that at least about a 1000-fold amplification is achieved. The amplified product is purified with a QIAquick PCR Purification Kit (Qiagen, Inc.), or like procedure, after which it is cleaved with Bbv I using the manufacturer's recommended protocol (New England Biolabs). After isolation by polyacrylamide gel electrophoresis and purification, the pairs are concatenated by carrying out a conventional ligation reaction. The concatenated fragments are separated by polyacrylamide gel electrophoresis and concatemers greater than about 200 basepairs are isolated and ligated into a Phagescript SK sequencing vector (Stratagene Cloning Systems, La Jolla, Calif.). Preferably, a number of clones are expanded and sequenced that ensure with a probability of at least 99% that all of the pairs of the aliquot are sequenced. A "lane" of sequence data (about 600 bases) obtained with conventional sequencing provides the sequences of about 25 pairs of segments. Thus, after transfection, a 1000 individual clones are expanded and sequenced on a commercially available DNA sequencer, e.g. PE Applied Biosystems model 377, to give the identities of about 25,000 pairs of segments.

EXAMPLE 2

Analysis of Human Pancreatic Cell Expression by Nla III Digestion of a cDNA Library Purified on Solid Phase Supports In this example, a cDNA library is constructed from human pancreatic mRNA available commercially from Clontech Laboratories (Palo Alto, Calif.). After first strand synthesis using a 5'-biotinylated poly(dT) primer, second strand synthesis is accomplished using random primers with a conventional protocol. After Sph I linkers are ligated to the cDNAs, they are affinity purified with avidinated magnetic bead, digested to completion with four-base cutter, Nla III, and the released fragments are purified and inserted into a pUC 19 cloning vector modified as described below for explansion and generation of pairs of sequence tags. The pairs of sequence tags are excised from the vector, ligated to form concatemers, cloned, and sequenced, as described in Example 1.

The following insert is prepared for ligation into an Eco RI-Hind III-digested pUC 19:

As above, after ligation, transformation of a suitable host, and expansion, the modified pUC19 is isolated and the insert is sequenced to confirm its identity.

5 μg of mRNA is converted into biotinylated cDNA using a conventional cDNA synthesis kit (Capture Clone Magnetic cDNA Synthesis and Ligation System, Promega Corp., Madison, Wis.), after which Sph I linkers (New England Biolabs, Beverly, Mass.) are ligated to the blunt ends of the cDNAs. The cDNAs are then affinity purified with avidinated magnetic beads following the manufacturer's suggested protocol. The bead-cDNA conjugates are resuspended in a cleavage buffer (NEBuffer 4 plus bovine serum albumin, New England Biolabs, Beverly, Mass.) for cleavage with Nla III (New England Biolabs) following the manufacturer's protocol (≈4–5 units Nla III incubated for 1 hour at 37° C.). After separating the beads from the reaction mixture, the released fragments are isolated by phenol extraction followed by ethanol precipitation. The fragments are then inserted into the above-modified Sph I-digested pUC 19. The procedure of Example 1 is followed thereafter so that concatemers of pairs are formed, cloned, and sequenced as described.

EXAMPLE 3

Analysis of Yeast Gene Expression by Sau 3A and Tsp 509

Digestion of a cDNA Library Followed by Adaptor Ligation After double stranded blunt-end cDNA is produced as described in Example 1, it is digested to completion with Sau 3A using the manufacturers (New England Biolabs) suggested protocol. The restriction fragments are removed from the reaction mixture by phenol extraction and ethanol precipitation, after which the precipitate is re-suspended in NEBuffer No. 1. 10 units of Tsp 509 is added to give a 50 μl reaction volume which is incubated at 65° C. for 1 hour. After phenol extraction and ethanol precipitation, the fragments are resuspended in T4 DNA ligase buffer, as described in Example I. The adaptors of Formula I are added to the reaction mixture in approximately 10-fold concentration excess over that of the fragments. T4 DNA ligase is added under conventional reaction conditions. After incubation, the adaptors are separated from the fragments by a commercially available anion-exchange column (Qiagen), and the isolated fragments are then digested to completion with Eco RI using the manufacturer's (New England Biolabs) recommended protocol. After isolation by phenol extraction and ethanol precipitation, the Eco RI fragments are inserted into the Eco RI cloning site of the pZErO-1 vector (Invitrogen, Carlsbad, Calif.) using the manufacturer's instructions. After transformation and selection, isolated vectors are treated to produced concatemers of pairs as described above.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

---

I claim:

1. A method of analyzing gene expression in a cell or tissue, the method comprising the steps of
    (a) forming a population of cDNA molecules from mRNA of a cell or tissue;
    (b) digesting the population of cDNA molecules with at least one restriction endonuclease to produce a population of polynucleotides having predetermined ends;
    (c) enzymatically removing a segment of nucleotides from each predetermined end of each polynucleotide and ligating the segments from each end together to form a pair of sequence stages for each polynucleotide, wherein said segments are formed by inserting each of said polynucleotides into a cloning site of a vector, the cloning site being flanked by a first type IIs restriction site and a second type IIs restriction site such that a type IIs restriction endonuclease recognizing either said first or second sites cleaves the vector within to said polynucleotide, the first IIs restriction site and the second type IIs restriction site being the same or different and each of the first and second type IIs restriction sites being unique to the vector;
    (d) determining the nucleotide sequences of a sample of pairs of sequence tags; and
    (e) tabulating the nucleotide sequences of the pairs of sequence tags to form a frequency distribution of gene expression in the cell or tissue.

2. The method of claim 1 wherein said step of determining said nucleotide sequences includes the steps of ligating said sample of pairs of sequence tags together to form one or more concatenations of pairs of sequence tags and sequencing the concatenations of pairs of sequence tags.

3. The method of claim 1 wherein said at least one restriction endonuclease is a four-cutter restriction endonuclease which leaves a four-nucleotide protruding strand after cleavage.

4. The method of claim 1 wherein said step of enzymatically removing further includes cleaving said vector with one or more nucleases recognizing said first IIs restriction site and said second type IIs restriction site to form a linearized vector having said segments of nucleotides at each end.

5. The method of claim 4 wherein said step of enzymatically removing further includes re-circularizing said linearized vector to form said pair of sequence tags.

6. A method of determining sequence frequencies in a population of polynucleotides, the method comprising the steps of:
    (a) providing a population of polynucleotides having predetermined ends;
    (b) inserting each polynucleotide of the population into a vector, the vector having at least one type IIs restriction endonuclease recognition site adjacent to each end of the inserted polynucleotide, each type IIs restriction endonuclease recognition site being oriented such that a type IIs restriction endonuclease recognizing said sites cleaves the vector within to the inserted polynucleotide;
    (c) cleaving each vector with one or more type IIs restriction endonucleases recognizing the type IIs restriction endonuclease recognition sites so that the vector is linearized and has a sequence tag of the inserted polynucleotide at each end;
    (d) re-circularizing the vector to form a pair of sequence tags for the inserted polynucleotide; and
    (e) determining the nucleotide sequence of each pair of sequence tags of a sample of re-circularized vectors to give the sequence frequencies of the population of polynucleotides.

7. The method of claim 6 further including the step of tabulating the pairs of nucleotide sequences of said sequence tags of said re-circularized vectors of said step (e) to form a frequency distribution of sequences in the population of polynucleotides.

8. The method of claim 7 wherein said step of determining said nucleotide sequence of each of said pairs of said sequence tags includes the steps of removing said pairs of said sequence tags from said re-circularized vectors of said sample, ligating the removed pairs of said sequence tags to form one or more concatenations of pairs, and sequencing the concatenations of pairs.

* * * * *

SEQUENCE LISTING

```
<160> NUMBER OF SEQ ID NOS:  9

<210> SEQ ID NO 1
<211> LENGTH: 22
<212> TYPE: DNA
<213> ORGANISM: Artificial Sequence
<220> FEATURE:
<221> NAME/KEY:
<222> LOCATION:
<223> OTHER INFORMATION: Single strand of adaptor

<400> SEQUENCE: 1
ggctaggaat tcattcgtgc ag                                              22
```

-continued

```
<210> SEQ ID NO 2
<211> LENGTH: 26
<212> TYPE: DNA
<213> ORGANISM: Artificial Sequence
<220> FEATURE:
<221> NAME/KEY:
<222> LOCATION:
<223> OTHER INFORMATION: Single strand of adaptor

<400> SEQUENCE: 2
aattctgcac gaatgaattc ctagcc                                    26

<210> SEQ ID NO 3
<211> LENGTH: 26
<212> TYPE: DNA
<213> ORGANISM: Artificial Sequence
<220> FEATURE:
<221> NAME/KEY:
<222> LOCATION:
<223> OTHER INFORMATION: Single strand of adaptor

<400> SEQUENCE: 3
gatcctgcac gaatgaattc ctagcc                                    26

<210> SEQ ID NO 4
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Single strand of adaptor

<400> SEQUENCE: 4
aattagccgt acctgcagca gtgcagg                                   27

<210> SEQ ID NO 5
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Single strand of adaptor

<400> SEQUENCE: 5
aattcctgca cagctgcgaa tcattcg                                   27

<210> SEQ ID NO 6
<211> LENGTH: 22
<212> TYPE: DNA
<213> ORGANISM: Artificial Sequence
<220> FEATURE:
<221> NAME/KEY:
<222> LOCATION:
<223> OTHER INFORMATION: Single strand of adaptor

<400> SEQUENCE: 6
agctcgaatg attcgcagct gt                                        22

<210> SEQ ID NO 7
<211> LENGTH: 32
<212> TYPE: DNA
<213> ORGANISM: Artificial Sequence
<220> FEATURE:
<221> NAME/KEY:
<222> LOCATION:
<223> OTHER INFORMATION: Single strand of adaptor
```

-continued

```
<400> SEQUENCE: 7
gcaggaattc ctgcactgct gcaggtacgg ct                            32

<210> SEQ ID NO 8
<211> LENGTH: 54
<212> TYPE: DNA
<213> ORGANISM: Artificial Sequence
<220> FEATURE:
<221> NAME/KEY:
<222> LOCATION:
<223> OTHER INFORMATION: Double stranded insert

<400> SEQUENCE: 8
aattagccgt acctgcagca gtgcaggaat tcctgcacag ctgcgaatca         50
ttcg                                                           54

<210> SEQ ID NO 9
<211> LENGTH: 54
<212> TYPE: DNA
<213> ORGANISM: Artificial Sequence
<220> FEATURE:
<221> NAME/KEY:
<222> LOCATION:
<223> OTHER INFORMATION: Double stranded insert

<400> SEQUENCE: 9
aattagccgt acctgcagca gtgcaggcat gcctgcacag ctgcgaatca         50
ttcg                                                           54
```